United States Patent
Jaeb et al.

(10) Patent No.: US 8,000,777 B2
(45) Date of Patent: Aug. 16, 2011

(54) SYSTEM AND METHOD FOR TRACKING HEALING PROGRESS OF TISSUE

(75) Inventors: Jonathan Paul Jaeb, Boerne, TX (US); Tianning Xu, Duluth, GA (US); Christopher Brian Locke, Bournemouth (GB); Mark Stephen James Beard, Ferndown (GB)

(73) Assignee: KCI Licensing, Inc., San Antonio, TX (US)

( * ) Notice: Subject to any disclaimer, the term of this patent is extended or adjusted under 35 U.S.C. 154(b) by 170 days.

(21) Appl. No.: 11/901,663

(22) Filed: Sep. 18, 2007

(65) Prior Publication Data

US 2008/0071162 A1    Mar. 20, 2008

Related U.S. Application Data

(60) Provisional application No. 60/845,993, filed on Sep. 19, 2006.

(51) Int. Cl.
*A61B 6/00* (2006.01)
*G06K 9/00* (2006.01)

(52) U.S. Cl. .......... 600/476; 382/128; 382/167
(58) Field of Classification Search .......... 600/407; 382/128, 167
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |

(Continued)

FOREIGN PATENT DOCUMENTS

AU    550575 A1    8/1982

(Continued)

OTHER PUBLICATIONS

International Search Report and Written Opinion dated Sep. 11, 2008; PCT International Application No. PCT/US07/20353.

(Continued)

*Primary Examiner* — Michael T Rozanski

(57) ABSTRACT

A system and method for analyzing tissue healing may include an image capture device and a reference color marker of a predetermined color. A processing unit may be in communication with the image capture device, and be configured to receive image data from the image capture device. The image data may include image of a tissue site and the reference color marker. At least one image parameter may be adjusted based on at least a portion of the image of the reference color marker to normalize the image data. The normalized image data may be presented to a clinician.

20 Claims, 4 Drawing Sheets

U.S. PATENT DOCUMENTS

| | | | |
|---|---|---|---|
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,651,743 A | 3/1987 | Stoller | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,852,675 A * | 12/1998 | Matsuo et al. | 382/167 |
| 6,071,267 A | 6/2000 | Zamierowski | |
| 6,135,116 A | 10/2000 | Vogel et al. | |
| 6,208,749 B1 | 3/2001 | Gutkowicz-Krusin et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2007/0053554 A1* | 3/2007 | Fayad et al. | 382/128 |
| 2008/0008370 A1* | 1/2008 | Chio | 382/128 |
| 2008/0260218 A1* | 10/2008 | Smith et al. | 382/128 |

FOREIGN PATENT DOCUMENTS

| | | |
|---|---|---|
| AU | 745271 | 4/1999 |
| AU | 755496 | 2/2002 |
| CA | 2005436 | 6/1990 |
| CN | 1333000 A | 1/2002 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 97/047235 | 12/1997 |
| WO | WO 99/13793 | 3/1999 |
| WO | WO 00/76398 A1 | 12/2000 |
| WO | WO 02/080764 A1 | 10/2002 |
| WO | WO 2006/106509 | 10/2006 |

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (copy and certified translation).

K.F. Jeter, T.E. Tintle, and M. Chariker, Managing Draining Wounds and Fistulae: "New and Established Methods," *Chronic Wound Care*, edited by D. Krasner (Health Management Publications, Inc., King of Prussia, PA 1990), pp. 240-246.

G. Živadinović, V. Ðukić, Ž. Maksimović, D. Radak, and P. Pška, "Vacuum Therapy in the Treatment of Peripheral Blood Vessels," *Timok Medical Journal* 11 (1986), pp. 161-164 (copy and certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax, " *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

Krouskop T.A., et al "A Noncontact Wound Measurement System", Journal of Rehabilitation Research and Development, vol. 39, No. 3, May/Jun. 2002.

\* cited by examiner

SYSTEM AND METHOD FOR TRACKING HEALING PROGRESS OF TISSUE

CROSS-REFERENCE TO RELATED APPLICATIONS

This Application claims priority to co-pending U.S. Provisional Patent Application Ser. No. 60/845,993 filed on Sep. 19, 2006, the entire contents of which are hereby incorporated by reference.

BACKGROUND OF THE INVENTION

1. Field of the Invention

The principles of the present invention generally relate to a system and method for measuring a rate of biological tissue healing. More specifically, the principles of the present invention relate to measuring rate of biological tissue healing by normalizing color of an image of a tissue site and identifying colors of tissue site (e.g., wound) areas that are associated with a phase of healing.

2. Description of the Related Art

The field of wound therapy has advanced in recent years. One of the advancements of wound healing therapy has been the development of vacuum assisted wound healing. The application of reduced or negative pressure to a wound has been clinically shown to improve blood flow at the wound or tissue site, increase tissue growth, reduce infection, and improve healing time. Caregivers and clinicians may use such vacuum assisted wound healing to treat a variety of chronic and acute wound types, such as pressure ulcers, diabetic wounds, abdominal wounds, partial-thickness burns, trauma wounds, flaps and grafts.

Background on Wounds and Wound Healing Processes

A wound is generally defined as a break in the epithelial integrity of the skin. Such an injury, however, may be much deeper, including the dermis, subcutaneous fat, fascia, muscle, and even bone. Proper wound healing is a highly complex, dynamic, and coordinated series of steps leading to tissue repair. Acute wound healing is a dynamic process involving both resident and migratory cell populations acting in a coordinated manner within the extra-cellular matrix environment to repair the injured tissues. Some wounds fail to heal in this manner (for a variety of reasons) and may be referred to as chronic wounds.

Following tissue injury, the coordinated healing of a wound will typically involve four overlapping but well-defined phases: hemostasis, inflammation, proliferation, and remodeling. Hemostasis involves the first steps in wound response and repair that are bleeding, coagulation, and platelet and complement activation. Inflammation peaks near the end of the first day. Cell proliferation occurs over the next 7-30 days and involves the time period over which wound area measurements may be of most benefit. During this time fibroplasia, angiogenesis, re-epithelialization, and extra-cellular matrix synthesis occur. The initial collagen formation in a wound typically peaks in approximately 7 days. The wound re-epithelialization occurs in about 48 hours under optimal conditions, at which time the wound may be completely sealed. A healing wound may have 15% to 20% of full tensile strength at 3 weeks and 60% of full strength at 4 months. After the first month, a degradation and remodeling stage begins, wherein cellularity and vascularity decrease and tensile strength increases. Formation of a mature scar often requires 6 to 12 months.

Efforts in the Related Art to Measure Wound Healing Processes

Because wound treatment can be costly in both materials and professional care time, a treatment that is based on an accurate assessment of the wound and the wound healing process can be essential. There are a few wound parameters that may assist a clinician in determining healing progress of a wound. For example, wound area and volume measurements may provide a clinician with knowledge as to whether or not a wound is healing and, if the wound is healing, how rapidly the wound is healing. Wound assessment is an important process to properly treating a wound as improper or incomplete assessment may result in a wide variety of complications. Infections at a tissue site that go untreated may result in permanent damage or even death to a patient.

While wound measurement is a parameter that is beneficial to a clinician to determine wound healing progress, the size of the wound may not provide a clinician with enough information to fully assess whether or how a wound is healing. For example, while a wound may reduce in size, certain parts of a wound may become infected. A clinician often examines wound tissue for its color and texture to determine how a wound is healing. Wound tissue includes a wound bed and periwound areas or wound edges. Health of a wound may be determined by color of tissue. Conversely, certain problems may be detected from the color of wound tissue. For example, normal granulation tissue has a beefy, red, shiny textured appearance and bleeds readily, whereas necrotic tissue (i.e., dead tissue) may either be yellow-gray and soft, generally known as "slough" tissue, or hard and black/brown in color, generally known as "eschar" tissue. A clinician may observe and monitor these and other wound tissues to determine wound healing progress of the overall wound and specific wound regions.

While consistent wound measurement is a factor for accurately determining changes in wound size, so too is measurement of different wound tissue. Although texture of wound tissue is indicative of wound healing, color can also be used. One problem with color of wound tissue is that colors can often be altered depending on lighting. For example, a wound under incandescent lighting may have a different color appearance from a wound under fluorescent lighting. Also, different clinicians may have different color perception. For example, one clinician may have strong color perception while another may be color blind in one or more colors, thereby providing both with different interpretation of color of wound tissue.

While a number of techniques have been developed to estimate the size of a wound, there are but a few techniques for measuring different types of wound tissue. One technique includes placing a clear film over a wound and using a soft-tipped pen to color different wound tissues on the film, thereby making a record of the wound tissues. This process may be repeated to record wound healing over time. This process also suffers due to lighting conditions, color sensitivity of clinicians, capability of a clinician to accurately draw on the clear film, and inherent problems from contacting the film onto the wound tissue. Another technique includes making an outline of the wound on the film, scanning the image into a computer, and then drawing an estimation of the different wound tissue on the computer. This technique also suffers from inaccuracy.

SUMMARY OF THE INVENTION

To enable a clinician to monitor wound healing by monitoring wound tissue in an accurate manner, the principles of the present invention provide a wound healing assessment system and process to enable a clinician to accurately assess wound healing. One embodiment provides for a reference color marker to be placed at a tissue site when capturing an image of the tissue site so that the reference color marker may be used by an image processing system to alter at least one image parameter, such as brightness, to normalize the color of the tissue site to be accurate with respect to images the same or different tissue sites. In one embodiment, once the tissue site is normalized, a clinician may select wound regions that have certain colors or texture associated with a stage of wound healing using a touch-sensitive electronic display or pointing device, such as a computer mouse. In addition or alternatively, the image processing system may identify one or more wound tissue regions that have a color within a range of colors or wavelengths. The identified wound tissue may thereafter be used to determine area of the wound tissue region(s), thereby providing a clinician with an accurate assessment of wound tissue that is associated with a healing stage. Multiple ranges of colors may be used to identify different wound tissue regions that are associated with different wound healing stages. The wound assessment process may be repeated to monitor the wound healing process over time.

One embodiment of a system for analyzing tissue healing may include an image capture device and a reference color marker of a predetermined color. A processing unit may be in communication with the image capture device, and be configured to receive image data from the image capture device. The image data may include image of a tissue site and the reference color marker. At least one image parameter may be adjusted based on at least a portion of the image of the reference color marker to normalize the image data. The normalized image data may be presented to a clinician.

One embodiment for analyzing tissue healing may include capturing an image including a tissue site and a reference color marker. At least one image parameter may be adjusted based on at least a portion of the image of the reference color marker to normalize color of the image. The color normalized image may be presented to a clinician.

Another embodiment for analyzing tissue healing may include capturing an image including a tissue site. A clinician may be enabled to define multiple regions of the image of the tissue site, where at least two of the regions of the image defining tissue type are at different stages of tissue healing. An area of each of the at least two regions of the image defining tissue type at different stages of tissue healing may be calculated and displayed for the clinician. A reference color marker may be utilized to provide for color normalization of the image of the tissue site.

DETAILED DESCRIPTION OF THE DRAWINGS

Figure 1A:
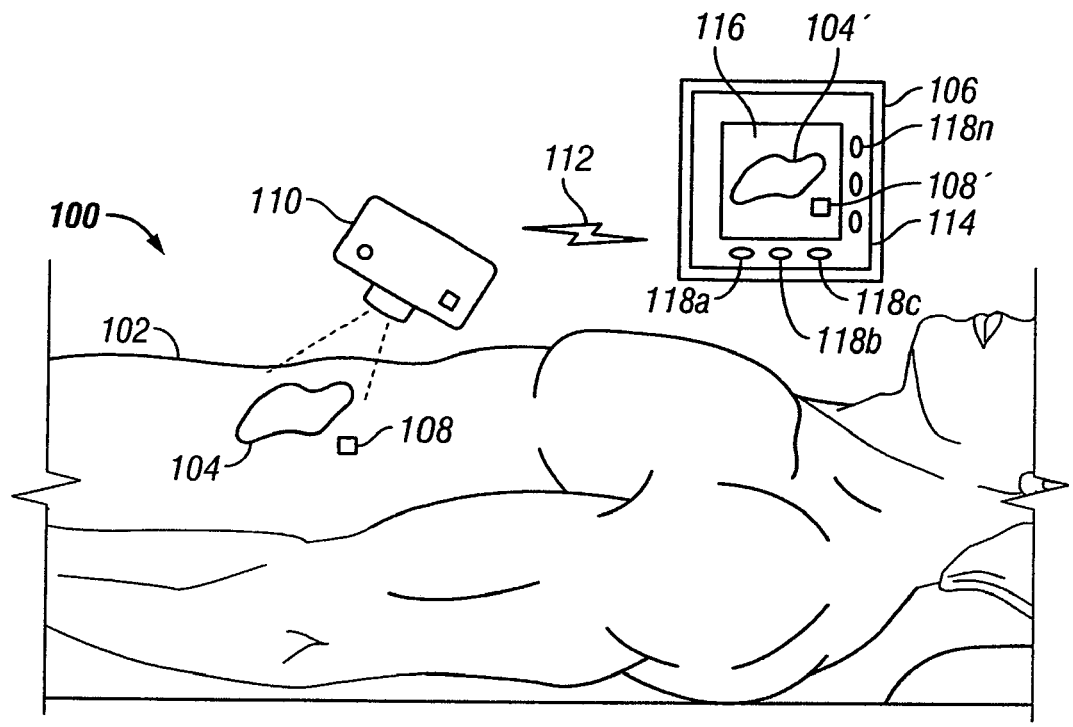
FIG. 1A is an illustration of an exemplary patient environment using a tissue treatment system in accordance with the principles of the present invention.

Referring to FIG. 1A, an exemplary patient environment showing a patient 102 having a tissue site 104 using a tissue treatment system 106 in accordance with the principles of the present invention. In one embodiment, the tissue treatment system 106 may be a vacuum assisted therapy device. Alternatively, the tissue treatment system 106 may be any system that is generally utilized to assist a patient in the process of tissue treatment, such as wound healing. Still yet, the tissue treatment system 106 may be any computing system that is configured to utilize software as described further herein to assist a caregiver or clinician with monitoring healing of the tissue site 104.

A color reference marker 108 is shown to be placed in association with the tissue site 104 so that an image capture device 110 may capture an image of both the tissue site 104 and color reference marker 108 in a photograph. The image capture device 110 may be a digital camera, mobile telephone, or any other electronic device configured to capture an image in a digital or analog format. In general, to expedite capturing and working with an image of the tissue site 104, a digital camera that is configured with a wireless communications link 112 with the tissue treatment system 106 may be used. The wireless communications link 112 may be an 802.11 wireless communications link or WiFi communications link. Any other wireless communications link protocol may be utilized. Alternatively or additionally, a wired connection may be made between the tissue treatment system 106 and the image capture device 110. Still yet, the image capture device 110 may utilize a memory device (not shown) that may be transferred between electronic devices. The memory device may include flash memory, mini-DVD, or any other memory device with which the tissue treatment system 106 may be compatible.

The term "tissue site" as used herein refers to a wound or defect located on or within any tissue, including but not limited to, bone tissue, adipose tissue, muscle tissue, neuro tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The term "clinician" is used herein as meaning any medical professional, user, family member of a patient, or patient who interacts or interfaces with a reduced pressure delivery system.

The color reference marker 108 is a device that is used by the tissue therapy system 106 for normalizing color of an image of the tissue site 104. The color reference marker 108 may be virtually any color, but one that the tissue treatment system 106 has been configured to use to normalize color of a tissue site. For example, the color reference marker 108 may be white, black, grayscale, Pantone matching system (PMS) spot color, two color, four color, or any other color combination. The term "color" is used herein to mean any color or any shade in any scale (e.g., grayscale). In addition, the color reference marker 108 may be paper, plastic, or any other material. In one embodiment, the color reference marker 108 is a sterilized material to avoid infecting the tissue site 104. The color reference marker 108 may further include an adhesive on one side to enable a clinician to adhere the color reference marker 108 to the patient 102 or an object within view of the tissue site 104 by the image capture device 110. Alternatively, the clinician may use a tape or other temporary fastener to locate the color reference marker 108 at or near the tissue site 104.

In terms of normalizing color of an image of the tissue site 104, the tissue treatment system 106 may import or otherwise receive an image of the tissue site 104 and color reference marker 108 captured by the image capture device 110. An electronic display 114 may be utilized to display an image 116 of the tissue site 104' and color reference marker 108'. In one embodiment, the electronic display 114 is a touch-sensitive electronic display that responds to a stylus (not shown) or finger to enable a clinician to interact with images and controls displayed on the electronic display 114.

Soft-buttons 118a-118n or other graphical control elements may be disposed on the electronic display 114 to enable the clinician to enter a mode, edit an image, or perform any other control as definable by a developer and executed by the tissue treatment system 106. For example, a soft-button 118a may enable a user to normalize the image 116 by correcting the color reference marker 108' to a predetermined color. Another soft-button 118b may cause the tissue treatment system 106 to enter a tissue trace mode to enable a clinician to trace a perimeter of a wound or other tissue site, thereby defining the tissue site. Another soft-button 118c may cause the tissue treatment system 106 to enter a tissue type trace mode, where a clinician may be able to define or otherwise identify various tissue types (e.g., eschar tissue) of the tissue site 104 by tracing or applying indicia at the perimeter of the different tissue types. Another soft-button 118n may provide for zooming in and out of the image. Another soft-button may enable saving the image to an image database on the tissue treatment system 106. It should be understood that any function to enable the clinician to collect, manipulate, edit, define tissue types, etc., may be provided on the tissue treatment system 106.

Figure 1B:
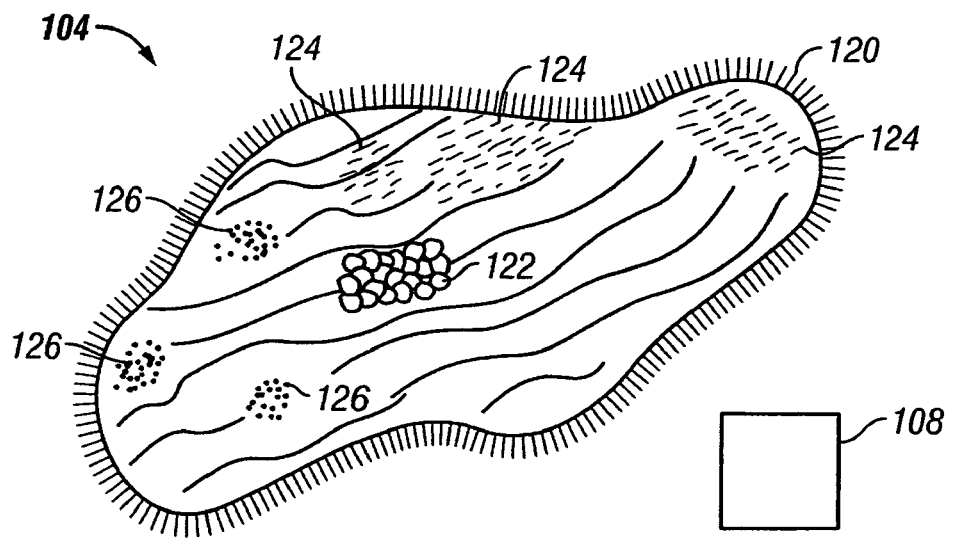
FIG. 1B is an illustration of an exemplary tissue site of a patient and color reference marker for use in normalizing an image of the tissue site.

Referring to FIG. 1B, the tissue site 104 of patient 102 and color reference marker 108 for use in normalizing an image of the tissue site are shown. The color reference marker 108 is shown to be white. However, the color reference marker 108 may be any color, as previously described. The tissue site 104 is shown to have a variety of tissue types. For example, wound edges or periwound skin 120 may be pink/white and define tissue site 104, granulation tissue 122 may be red/deep pink that is moist with a bumpy appearance, necrotic tissue 124 may be black/brown in color and be hard, and slough tissue 126 may be yellow/white in color and be loose. It should be understood that other tissue types that occur during wound or tissue healing may be identified by color or texture. By including the color reference marker 108 in an image of the tissue site 104, adjustment to image of the color reference marker 108 may adjust color of the image of the tissue site to be normalized.

The tissue treatment system 106 may be configured to perform color adjustment on an entire image based on at least a portion of a collected image of the reference color marker 108. The reference color marker 108 may be a predefined or predetermined color and adjustment of the image may include changing the image of reference color marker 108 until the image substantially matches the predetermined color. Being substantially matched to a predetermined color may be that each color component is within 1% of a predetermined color percentage value for respective color components, such as red 18%+/−1%, green 27%+/−1%, and blue 40%+/−1%, if an RGB color scheme is used. Alternatively, being substantially matched to a predetermined color may be that the aggregate color formed by color components is within 3% of a predetermined color (e.g., a PMS spot color, such as Blue PMS-300, if a four color PMS color scheme is used). The tissue treatment system 106 may be calibrated such that when an image of the reference color marker 108 is color adjusted to substantially match a predefined color (e.g., pure white), the image of the tissue site 104 is normalized. Adjustment of color may be performed in a variety of manners, as understood in the art. In accordance with the principles of the present invention, adjustment of color may include changing brightness, contrast, hue, saturation, color balance, color level, or any other adjustment that alters the image of the reference color marker 108. For example, if the reference color marker 108 is white, a white balance, which is a process of removing colors so that an object, such as the reference color marker 108, that is true white appears true white in an image. If, for example, incandescent light is used to light a wound, the reference color marker 108, which may be white, captures the incandescent light and the color caused by the incandescent light is removed from the image of the reference color marker 108 until the image of the reference color marker 108 is white within a predetermined tolerance. The color adjustment of the reference color marker 108 may be applied to the image of the tissue site, thereby normalizing the color of the tissue site. By normalizing the color of the tissue site, lighting conditions that may vary over time, between rooms, between facilities, etc., are factored out.

Figure 2:
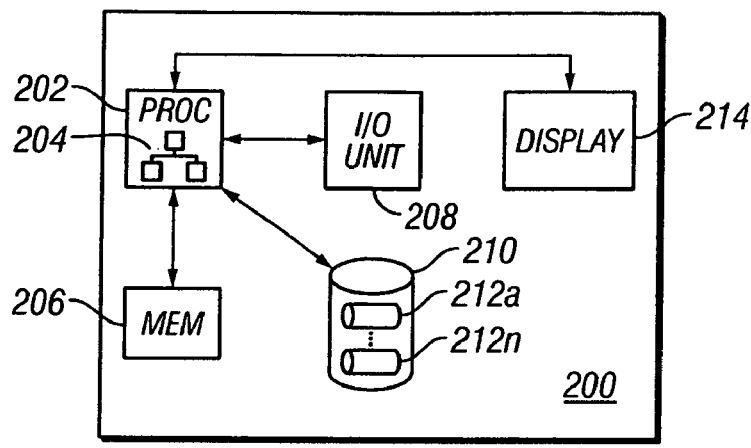
FIG. 2 is a block diagram of an exemplary processing system for use in generating images and defining and normalizing tissue color.

Referring to FIG. 2, an exemplary processing system 200 for use in generating images and defining and normalizing tissue site color is shown. The processing system 200 may include a processing unit 202 that executes software 204. The processing unit 202 may be configured with one or more processors that are the same or different types. For example, the processing unit 202 may include a general processing unit and a digital signal processing unit configured to perform image processing to perform color adjustments in accordance with the principles of the present invention.

The processing unit 202 may further be in communication with (i) a memory 206 for storing data and software code, (ii) input/output (I/O) unit 208 for communicating with other devices and systems, such as a digital camera, wirelessly, via a wire, or via a memory input device (not shown), (iii) storage unit 210 that may store one or more data repositories 212a-212n (collectively 212), such as a database having one or more files, and (iv) electronic display 214 that may or many not be touch-sensitive. The software 204 may be configured to interface with each of the other devices (e.g., electronic display 214) to perform tissue site image collection, for example, and color adjust the image of the tissue site by adjusting color for an image of a reference color marker.

Figure 3:
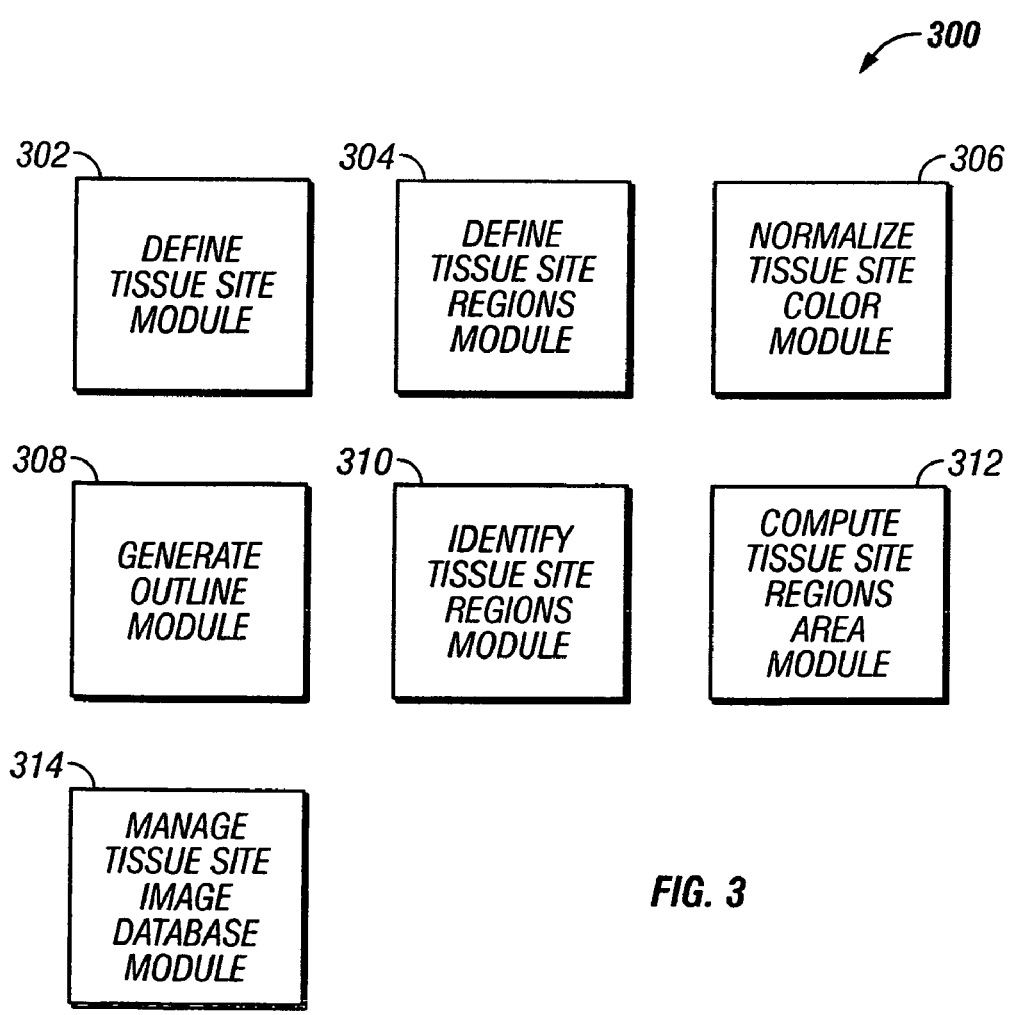
FIG. 3 is a block diagram of exemplary software modules executable by the processing system of FIG. 2 to perform tissue defining and color adjustment functions in accordance with the principles of the present invention.

Referring now to FIG. 3, software modules 300 of software 204 (FIG. 2) executable by processing unit 202 (FIG. 2) may be utilized to perform wound defining and color adjustment functions in accordance with the principles of the present invention. The software modules 300 shown are exemplary and may include additional and/or other software modules to provide the same or similar functionality.

Define tissue site module 302 is a software module that may be configured to enable a clinician to display an image of a tissue site and either trace or identify consecutive locations on a perimeter of a tissue site using a touch-sensitive electronic display or pointing device (e.g., computer mouse) and estimate a trace of the perimeter between each of the consecutive locations on the perimeter. The area within the trace or estimated trace defines the tissue site, which, in one embodiment, may be a wound.

Define tissue site regions module 304 is a software module that may be configured to enable a clinician to define one or more sub-regions within the tissue site defined by the define tissue site module. In defining the sub-region(s), the clinician may trace perimeter(s) of the sub-region(s) being displayed on an electronic display or otherwise cause the perimeter(s) to be defined. The tissue site regions, or sub-regions of the tissue site, may be the same or different tissue types that have developed as different stages of tissue healing. For example, the tissue site regions may include necrotic or slough tissue. In another embodiment, the define tissue site regions module 304 may be configured to automatically or semi-automatically locate tissue type in the same or similar tissue healing stage by searching for any tissue within a color or wavelength range that defines the tissue healing stage. For example, the clinician may identify a color of tissue in the image of the tissue site and the module 304 may locate all of the tissue within the tissue site that is within a percentage color range using individual colors (e.g., red, green, blue parameters having a total percentage value within a predetermined range, such as 2 percent), brightness, or other image parameter that identifies the tissue to be within the same tissue healing stage. A trace may be created around the tissue regions located by the module 304 estimated to be within the same tissue healing stage.

Normalize tissue site color module 306 is a software module that may be configured to normalize color of an image of a tissue site based on color adjustment to at least a portion of an image of a reference color marker to substantially match a predetermined color, as previously described herein.

Generate outline module 308 is a software module that may be configured to generate an outline of a tissue site or tissue region within a tissue site based on selected locations by a clinician to define the tissue site or tissue region. The generate outline module 308 may also be used if the clinician performs a trace, but to a lesser extent and, optionally, to determine points or smoothen the trace.

Identify tissue site regions module 310 is a software module that may be configured to generate curvilinear lines (i.e., lines that may have straight and curved portions) to highlight or otherwise define tissue site regions. In addition, the identify tissue site regions module 310 may be utilized to generate a graphical image, such as a solid color, that is opaque or translucent to show a clinician the area(s) of a tissue site region. In one embodiment, different colors, patterns, or other graphical image may be utilized to identify different tissue types (e.g., necrotic tissue with brown or black graphical image versus granulation tissue with red graphical image).

Compute tissue site regions area module 312 is a software module that may be configured to compute area of one or more tissue site regions of the same or different tissue types. By determining area of tissue site regions, a clinician can monitor healing or treatment progress of a tissue site over time. In one embodiment, the software may enable for a tissue site depth to be entered and the module 312 may generate a tissue site volume value. The tissue site area and/or volume may be displayed on the electronic display, optionally within a tissue site region, along with the image of the tissue site and tissue site regions.

Manage tissue site image database module 314 is a software module configured to store tissue site images in one or more databases. The module 314 may be configured to store images associated with patients, by date, by tissue site type (e.g., wound), by treatment identifier, by clinician, or by any other identifier. The module 314 may store each captured image separately from traces, graphical images that over or underlay the image of the tissue site, calculated tissue site area and volume, date and time information, or any other information other than the image so that a clinician may retrieve the raw tissue site images without any other information, and the other information may be stored in association with the tissue site images so that the information can be retrieved simultaneously or separately. In one embodiment, the information associated with the tissue site images may be stored in a table or other format to enable a clinician to perform searches, sorts, tabulations, or any other database function. Still yet, the module 314 may store raw and color normalized tissue site images.

Figure 4:
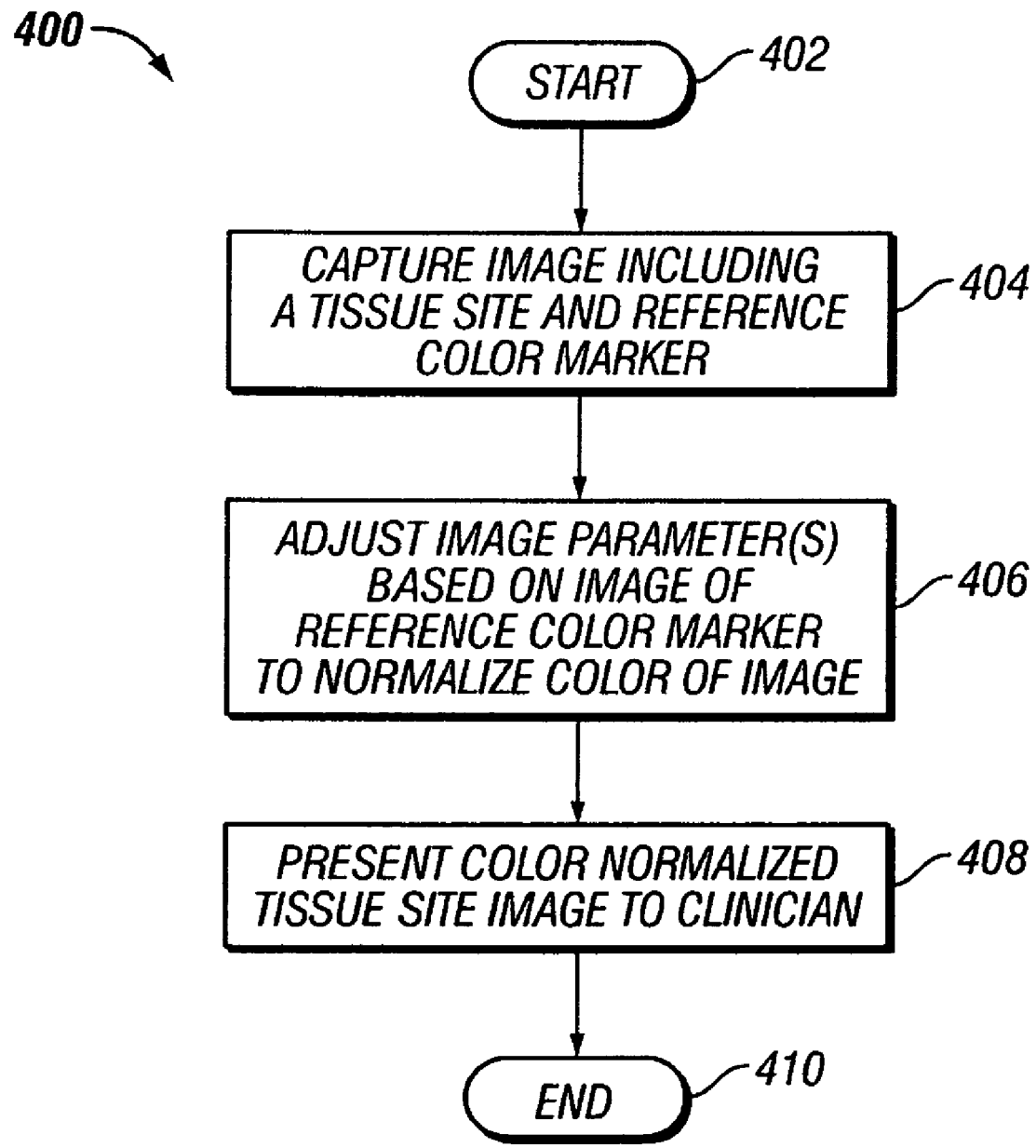
FIG. 4 is a flow diagram of an exemplary process for performing a color adjustment function to normalize color of a tissue site.

Referring to FIG. 4, a process 400 for performing a color adjustment function to normalize color of a tissue site is presented. The process 400 starts at step 402 and at step 404, an image including a tissue site and reference color marker may be captured. The reference color marker may be any color, such as white, and be used to normalize color of the tissue site to offset lighting when the image of the tissue site is captured. At step 406, one or more image parameters may be adjusted based on at least a portion of the image of the reference color marker to normalize color of the image. The adjustment may be any color adjustment to cause the image of the reference color marker to be within a range or tolerance of or substantially match a predefined color tolerance (e.g., pure white (i.e., yellow, cyan, magenta, and black values at 0%) +/−1% of any color component). Other range percentages may be utilized in accordance with the principles of the present invention. By adjusting the image (or portion of the image) of the tissue site, the tissue site may be color normalized to remove lighting conditions in the room that the image of the tissue site is captured. At step 408, the color normalized tissue site image is presented to the clinician. The process ends at step 410. In one embodiment, the clinician may use the color normalized tissue site image to define the tissue site by tracing around the perimeter of the tissue site. Alternatively, a software module that locates an edge between different colors or textures of the tissue site may estimate the perimeter of the tissue site. In adjusting the color, the color may be adjusted using one or more different image correction techniques, including white balancing, adjustment to hue, brightness, or other color adjustment function as understood in the art.

Figure 5:
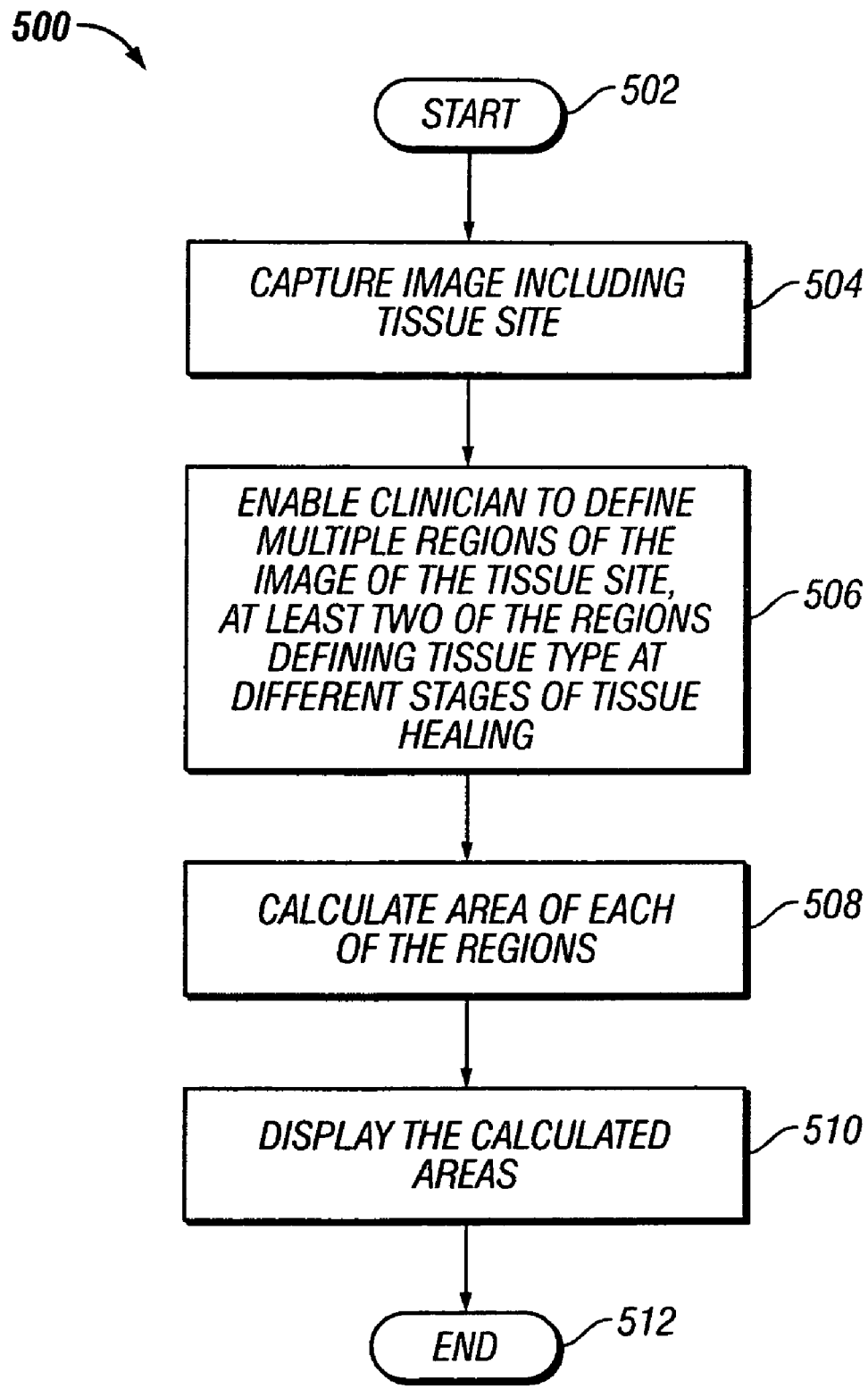
FIG. 5 is a flow diagram of an exemplary process for analyzing a tissue site.

Referring to FIG. 5, a process 500 for analyzing tissue healing is shown. The process 500 starts at step 502. At step 504, an image including a tissue site may be captured. At step 506, a clinician may be enabled to define multiple regions of the image of the tissue site, where at least two of the regions of the image defining tissue type are at different stages of tissue healing. An area of each of the regions of the image defining tissue type at different stages of tissue healing may be calculated at step 508. The calculated areas may be displayed at step 510. The process ends at step 512. A reference color marker may be utilized to provide for color normalization of the image of the tissue site.

Although the principles of the present invention have been described in terms of the foregoing embodiments, this description has been provided by way of explanation only, and is not intended to be construed as a limitation of the invention. Those skilled in the art will recognize modifications of the present invention that might accommodate specific patient and tissue treatment environments.

We claim:

1. A system for analyzing tissue healing, said system comprising:
   an image capture device;
   a reference color marker of a predetermined color;
   a processing unit in communication with said image capture device, and configured to:
      receive image data from said image capture device, the image data including image of a tissue site and said reference color marker;
      determine an image color adjustment by adjusting the image of the reference color marker to the predetermined color;
      apply the image color adjustment to the image of the tissue site to normalize the image of the tissue site to generate a normalized image;
      compare colors of the tissue site in the normalized image to a first range of colors defining a first tissue type for identifying a particular first type of tissue at the tissue site;
      compare colors of the tissue site in the normalized image to a second range of colors defining a second tissue type for identifying a second type of tissue at the tissue site, the first and second tissue types being tissue in different stages of healing;
      identify the first and second tissue types; and
      present the normalized image to a clinician.

2. The system according to claim 1, wherein said processing system is further configured to:
   enable the clinician to identify at least one region of the first tissue type of the tissue site that is within a stage of tissue healing by highlighting the at least one region.

3. The system according to claim 2, wherein the at least one highlighted region of the tissue site defines necrotic tissue, granulation tissue, or slough tissue.

4. The system according to claim 2, wherein said processing unit is further configured to calculate area of the at least one region of the tissue site.

5. The system according to claim 4, further comprising an electronic display, wherein said processing unit is further configured to display the tissue site and identify the region of the tissue site within the tissue healing stage on said electronic display.

6. The system according to claim 2, wherein enabling the clinician to identify the at least one region by highlighting the at least one region includes enabling the clinician to generate a border around the at least one region of the tissue site.

7. The system according to claim 1, wherein said processing unit is further configured to:
   determine area of at least one region of the tissue site that is within a first tissue healing stage; and
   determine area of at least one region of the tissue site within a second tissue healing stage.

8. The system according to claim 7, wherein said processing unit is further configured to, in response to a user selecting a color of tissue in the normalized image, identify all of the tissue within the tissue site that is within a color range percentage of the selected color.

9. The system according to claim 1, wherein said reference color marker is a card.

10. The system according to claim 1, wherein said reference color marker is white.

11. The system according to claim 10, wherein said processing unit is further configured to adjust at least one image parameter based on at least a portion of the image of said reference color marker to normalize the image data, and wherein the at least one image parameter includes a white balance image parameter.

12. A method for analyzing tissue healing, said method comprising:
   capturing an image including a tissue site and a reference color marker of a predetermined color;
   determining an image color adjustment by adjusting the image of the reference color marker to the predetermined color;
   applying the image color adjustment to the image of the tissue site to normalize the image of the tissue site to generate a normalized image;
   automatically comparing colors of the tissue site in the normalized image to a first range of colors defining a first tissue type for identifying a first type of tissue at the tissue site;
   automatically comparing colors of the tissue site in the normalized image to a second range of colors defining a second tissue type for identifying a second type of tissue at the tissue site, the first and second tissue types being in different stages of healing;
   identifying the first and second tissue types; and
   presenting the normalized image to a clinician.

13. The method according to claim 12, further comprising enabling the clinician to identify at least one region of the first tissue type of the tissue site that is within a stage of tissue healing by highlighting the at least one region.

14. The method according to claim 13, wherein enabling the clinician to identify at least one region of the first tissue type of the tissue site by highlighting the at least one region of the tissue site includes enabling the clinician to identify that the at least one region of the tissue site is necrotic tissue, granulation tissue, or slough tissue.

15. The method according to claim 13, further comprising calculating area of the at least one region of the first tissue type of the tissue site.

16. The method according to claim 15, further comprising displaying the tissue site and identifying the at least one region of the tissue site within the tissue healing stage on the displayed tissue site.

17. The method according to claim 13, wherein enabling the clinician to identify at least one region of the tissue site by highlighting the at least one region of the tissue site includes enabling the clinician to generate a border around the at least one region of the tissue site.

18. The method according to claim 12, further comprising:
   determining area of at least one region of the tissue site that is within a first tissue healing stage; and
   determining area of the at least one region of the tissue site within a second tissue healing stage.

19. The method according to claim 18, further comprising in response to a user selecting a color of tissue in the normalized image, identifying all of the tissue within the tissue site that is within a color range percentage from the selected color.

20. The method according to claim 12, wherein capturing an image including a reference color marker includes capturing an image of a white reference color marker.

* * * * *

UNITED STATES PATENT AND TRADEMARK OFFICE
CERTIFICATE OF CORRECTION

| | | |
|---|---|---|
| PATENT NO. | : 8,000,777 B2 | Page 1 of 1 |
| APPLICATION NO. | : 11/901663 | |
| DATED | : August 16, 2011 | |
| INVENTOR(S) | : Jaeb et al. | |

It is certified that error appears in the above-identified patent and that said Letters Patent is hereby corrected as shown below:

column 9, line 24: the phrase — "identifying a particular first type of tissue site" should be changed to --identifying a first type of tissue at the tissue site--

Signed and Sealed this
Fourth Day of October, 2011

David J. Kappos
*Director of the United States Patent and Trademark Office*